United States Patent [19]

Cooper et al.

[11] 4,224,442
[45] Sep. 23, 1980

[54] 7-UREIDO ACETAMIDO SUBSTITUTED CEPHALOSPORIN ANTIBIOTICS

[75] Inventors: Robin D. G. Cooper; David K. Herron, both of Indianapolis, Ind.

[73] Assignee: Eli Lilly and Company, Indianapolis, Ind.

[21] Appl. No.: 553,062

[22] Filed: Mar. 3, 1975

Related U.S. Application Data

[63] Continuation-in-part of Ser. No. 456,516, Apr. 1, 1974, abandoned.

[51] Int. Cl.$^2$ .................. C07D 501/56; C07D 501/54; A61K 31/545
[52] U.S. Cl. ........................ 544/27; 544/26; 544/28; 544/30; 424/246
[58] Field of Search ............ 260/243 CN, 80; 544/26, 544/27, 28, 29, 30

[56] References Cited

U.S. PATENT DOCUMENTS

| | | | |
|---|---|---|---|
| 3,673,183 | 6/1972 | Erickson | 260/243 CN |
| 3,687,949 | 8/1972 | Holdrege | 544/30 X |
| 4,086,340 | 4/1978 | Schröck et al. | 424/246 |
| 4,093,722 | 6/1978 | Schröck et al. | 424/246 |
| 4,107,304 | 8/1978 | Schröck et al. | 424/246 |

FOREIGN PATENT DOCUMENTS

| | | | |
|---|---|---|---|
| 816238 | 12/1974 | Belgium | 544/30 |
| 7407815 | 12/1974 | Netherlands | 260/243 C |

*Primary Examiner*—Donald G. Daus
*Assistant Examiner*—Diana G. Rivers
*Attorney, Agent, or Firm*—William B. Scanlon; Arthur R. Whale

[57] ABSTRACT

Cephalosporin antibiotics of the formula

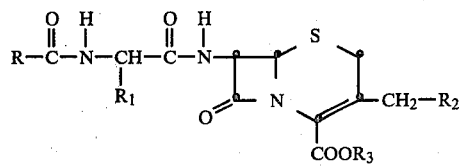

wherein R is

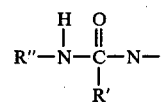

and R″ is H, $C_1$–$C_3$ alkyl, allyl, propargyl, $C_3$–$C_6$ cycloalkyl, phenyl, benzyl or furfuryl; R′ is H or methyl; or R is a cyclic urea group for example, R is

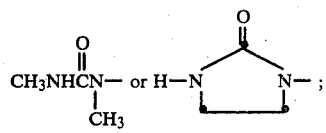

$R_1$ is phenyl, thienyl, or furyl; $R_3$ is a lower alkyl substituted 1H-tetrazole-5-thio or 1,3,4-thiadiazole-5-thio group and $R_4$ is hydrogen or an active ester group, e.g., an acetoxymethyl group; are highly active broad spectrum antibiotics especially useful in the treatment of infections attributable to the gram-negative microorganisms.

20 Claims, No Drawings

7-UREIDO ACETAMIDO SUBSTITUTED CEPHALOSPORIN ANTIBIOTICS

CROSS REFERENCE TO RELATED APPLICATION

This application is a continuation-in-part application of co-pending application Ser. No. 456,516 filed Apr. 1, 1974, now abandoned.

SUMMARY

Cephalosporin compounds having a high level of activity against both gram-negative and gram-positive pathogens are prepared by acylating the free amino group in the 7-position side chain of cephaloglycin, 7-(D-α-amino-α-phenylacetamido)-3-(1-lower alkyl-1H-tetrazole-5-ylthiomethyl)-3-cephem-4-carboxylic acid and 7-(D-α-amino-α-phenylacetamido)-3-(5-lower alkyl-1,3,4-thiadiazole-2-ylthiomethyl)-3-cephem-4-carboxylic acid and hydroxy and halogen derivatives thereof, with the carbamoyl chloride

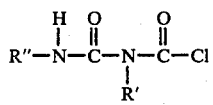

wherein R″ is H, allyl, propargyl, $C_3$–$C_6$ cycloalkyl, phenyl, benzyl or furfuryl, and R′ is H or methyl, or the cyclic carbamoyl chloride

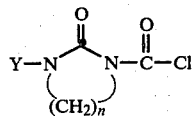

wherein Y is $CH_3SO_2$—, $CH_3C(O)$— or H and n is 2 or 3; or with the p-nitrophenyl carbamate

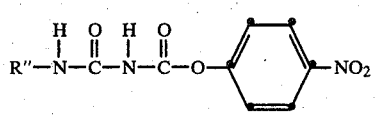

For example, 7-[D-α-(3-methylcarbamoyl-3-methyl-1-ureido)-α-phenylacetamido]-3-(1-methyl-1H-tetrazole-5-ylthiomethyl)-3-cephem-4-carboxylic acid is prepared by acylating 7-(D-α-amino-α-phenylacetamido)-3-(1-methyl-1H-tetrazole-5-ylthiomethyl)-3-cephem-4-carboxylic acid with N-methylcarbamoyl-N-methylcarbamoyl chloride. The new cephalosporins described herein are active against a broad spectrum of microorganisms, notably the gram-negative microorganisms and are accordingly useful in combating infections in warm blooded animals when administered parenterally.

The cephalosporins described herein can be converted to biologically active esters, for example, the acetoxymethyl or benzoyloxymethyl esters and to the pharmaceutically useful salts such as the sodium and potassium salts.

DESCRIPTION OF THE PRIOR ART

Cephalosporin compounds having a ureido or a substituted ureido substituent in the α-position of the 7-acylamido side chain have been described. In U.S. Pat. No. 3,673,183 issued June 27, 1972, and British Pat. No. 1,337,000, α-ureidocephalosporanic acids are disclosed. Acyloxymethyl esters of α-ureidocyclohexadienylacetamidocephalosporins are described in U.S. Pat. No. 3,708,479 and of α-aminobenzylpenicillin in U.S. Pat. No. 3,697,507. Penicillins and cephalosporins having an α-(3-imidoylureido)arylacetamido side chain are described in U.S. Pat. Nos. 3,634,405 and 3,646,024, respectively. In Belgian Pat. No. 767,647 α-3-acylureidobenzylpenicillins are disclosed wherein a wide variety of acyl groups are attached to the terminal nitrogen of the α-ureido group of the 6-arylacetamido side chain.

DETAILED DESCRIPTION

This invention relates to new cephalosporin antibiotic compounds represented by the following general formula

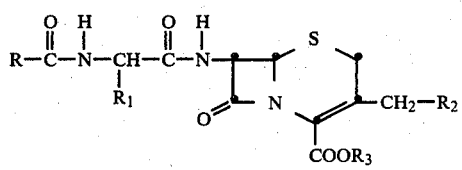

wherein
R is a 3-substituted ureido group represented by the formula

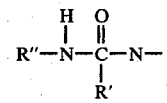

wherein R″ is hydrogen, $C_1$–$C_3$ alkyl, allyl, propargyl, $C_3$–$C_6$ cycloalkyl, phenyl, benzyl, or furfuryl; R′ is hydrogen or methyl;
or R is a cyclic ureido group of the formula

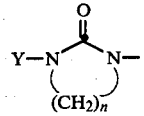

wherein
Y is hydrogen, acetyl or methanesulfonyl, and
n is 2 or 3;
$R_1$ is phenyl, mono- or dihydroxyphenyl, mono- or dihalophenyl, monohydroxy substituted mono- or dihalophenyl,

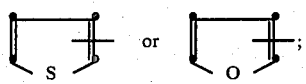

$R_2$ is acetoxy,

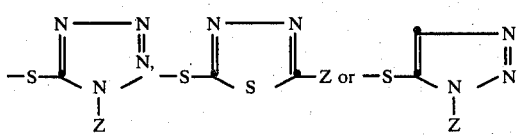

wherein Z is $C_1$–$C_4$ lower alkyl;

R₃ is hydrogen, indanyl, phthalidyl, an acyloxymethyl group of the formula

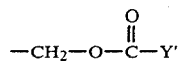

wherein
Y' is C₁–C₄ alkyl or phenyl, and when
R₃ is hydrogen, the pharmaceutically acceptable nontoxic salts thereof.

In the foregoing definition, the cyclic ureido groups represented are the five-membered imidazolidine-2-one-1-yl group (n=2) and the six-membered hexahydropyrimidine-2-one-1-yl group represented by the formulae

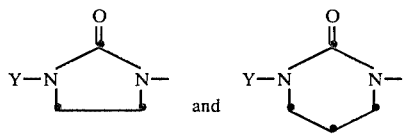

wherein Y is H—, CH₃SO₂— or CH₃C(O)—.

The term "halogen" as used herein refers to fluoro, chloro, and bromo and preferably chloro.

Representative of the substituted phenyl groups, (R₁) hydroxyphenyl, halophenyl, and hydroxy substituted halophenyl are 4-chlorophenyl, 4-bromophenyl, 3-fluorophenyl, 4-hydroxyphenyl, 3-hydroxyphenyl, 3-chloro-4-hydroxyphenyl, 2-chlorophenyl, 3,4-dichlorophenyl, 3,5-dichlorophenyl, 3,5-dihydroxyphenyl, 2-hydroxyphenyl, 4-hydroxy-3,5-dichlorophenyl, and 4-hydroxy-3,5-dibromophenyl.

The term "C₁–C₄ lower alkyl", represented by Z in the above formula, refers to methyl, ethyl n-propyl, isopropyl, n-butyl, t-butyl, and like straight and branched chain C₄ hydrocarbon radicals.

The term C₃–C₆ cycloalkyl refers to cyclopropyl, cyclobutyl, cyclopentyl and cyclohexyl.

The cephalosporin antibiotic compounds represented by the formula I, when R₃ is hydrogen, are prepared by acylating a 7-(D-α-amino-α-arylacetamido)-3-cephem-4-carboxylic acid represented by the formula II,

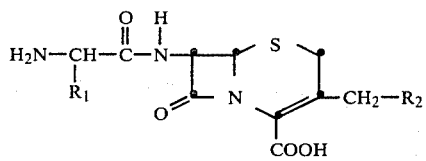

wherein R₁ and R₂ have the previously defined meanings.

The compounds of formula I wherein R is the 1,3-disubstituted ureido group

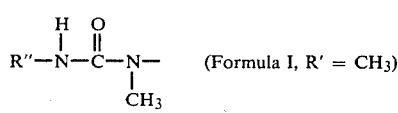

and R″ is other than hydrogen are prepared by acylating the cephalosporin compound II with the corresponding carbamoyl chloride,

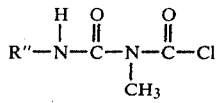

The compounds of the formula I wherein R is a cyclic ureido group are prepared by the acylation of II with a cyclic ureido carbamoyl chloride of the formula

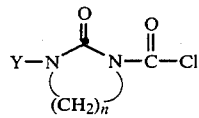

The compounds of the formula I wherein R is a 3-substituted ureido group

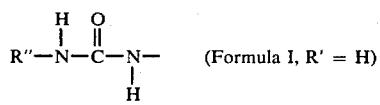

are prepared by the acylation of II with a p-nitrophenyl carbamate

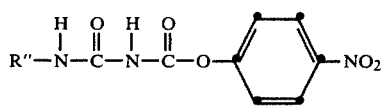

The starting materials represented by the formula II wherein R₁ is a phenyl, substituted phenyl, or thienyl group and R₂ is a 1-lower alkyl-1H-tetrazole-5-yl group or a 5-lower alkyl-1,3,4-thiadiazole-2-yl group are described by Ryan in U.S. Pat. No. 3,641,021. Compounds of the formula II wherein R₁ is a furyl group are prepared by the acylation of a 7-amino nucleus compound of the formula

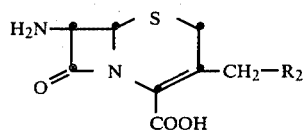

with the anhydride formed with α-(t-butyloxycarbamido)-furanacetic acid and isobutylchloroformate. Following the acylation the t-butyloxycarbonyl protecting group is removed by known methods, for example, with trifluoroacetic acid in the cold, or alternatively with p-toluenesulfonic acid in acetonitrile as described by Chauvette in U.S. Pat. No. 3,769,281.

The starting materials represented by formula II wherein R₂ is the acetoxy group are prepared by the acylation of 7-aminocephalosporanic acid with a phenyl, thienyl, or furyl glycine. The compound of the formula II wherein R₁ is phenyl and R₂ is acetoxy is the well known antibiotic, cephaloglycin.

The acylation of a compound of the formula II with the 1,3-disubstituted-ureidocarbamoyl chloride

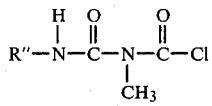

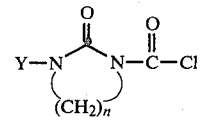

or the cyclic ureidocarbamoyl chloride involves the acylation of the free α-amino group in the 7-position side chain. The acylation is carried out in an inert solvent in the presence of a hydrogen halide acceptor at a temperature between about −5° C. and 20° C. and preferably at about 0°–5° C. Solvents such as acetonitrile, tetrahydrofuran, dimethylformamide and dimethylacetamide can be used in the acylation. A preferred solvent is acetonitrile. Should the starting material be insoluble or partly insoluble in the solvent, it can be solubilized by the addition of a silylating agent such as bis-(trimethylsilyl)acetamide (BSA) before the addition of the carbamoyl chloride.

Hydrogen halide acceptors which can be used include the tertiary amines such as triethylamine and pyridine and the alkylene oxides such as propylene oxide or butylene oxide.

The carbamoyl chlorides

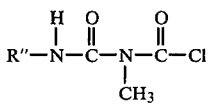

are prepared by reacting the 1,3-disubstituted urea with phosgene in a dry, inert solvent such as dichloroethane, dichloromethane or tetrahydrofuran. The reaction is preferably carried out in the cold at about 0°–5° C.

The symmetrical 1,3-dimethylurea affords but one carbamoyl chloride, namely, N-methylaminocarbonyl-N-methylcarbamoyl chloride

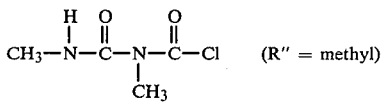

since both nitrogen atoms of the urea are equivalent.

The unsymmetrical ureas, wherein R″ is a group other than methyl, can form two carbamoyl chlorides on reaction with phosgene. The desired N-methylcarbamoyl chloride

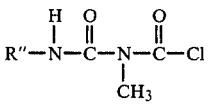

is separated from the undesired isomeric chloride by fractional crystallization from mixtures of polar and non-polar organic solvents such as mixtures of diethyl ether and petroleum ether, and acetone or ethyl acetate mixed with hexane or petroleum ether.

The 1,3-disubstituted ureas are prepared by well known methods or are commercially available.

Illustrative N-substituted-aminocarbonyl-N-methylcarbamoyl chlorides are represented by the foregoing formula wherein R″ is ethyl, $H_2C{=}CH{-}CH_2{-}$(allyl), $HC{\equiv}C{-}CH_2{-}$(propargyl), phenyl, benzyl, 2-furfuryl, cyclopropyl and cyclohexyl.

The cyclic ureido carbamoyl chlorides wherein Y and n are as defined above are prepared by reacting the substituted (Y=acetyl or methylsulfonyl) or unsubstituted (Y=H), imidazolidine-2-one(n=2) or hexahydropyrimidine-2-one(n=3) with phosgene in a dry, inert solvent at about 0°–10° C.

The cyclic ureido carbamoyl chlorides used to prepare the cephalosporins of the formula I are imidazolidine-2-one-1-ylcarbonyl chloride, 3-(methylsulfonyl)-imidazolidine-2-one-1-ylcarbonyl chloride, hexahydropyrimidine-2-one-1-ylcarbonyl chloride, 3-(methylsulfonyl)-hexahydropyrimidine-2-one-1-ylcarbonyl chloride, and 3-(acetyl)hexahydropyrimidine-2-one-1-ylcarbonyl chloride.

The preparation of the compounds represented by the formula 1 wherein $R_3$ is hydrogen and R′ is $CH_3$ is illustrated by the following description of the preparation of 7-[α-(3-methylcarbamoyl-3-methyl-1-ureido)-α-phenylacetamido]-3-(1-methyl-1H-tetrazole-5-ylthiomethyl)-3-cephem-4-carboxylic acid. 7-(D-α-Amino-α-phenylacetamido)-3-(1-methyl-1H-tetrazole-5-ylthiomethyl)-3-cephem-4-carboxylic acid is suspended in acetonitrile containing an excess of propylene oxide. A small excess of bis-(trimethylsilyl)acetamide is added to the suspension with stirring to effect solution. The solution is cooled to about 5° C. and a molar equivalent of N-methylaminocarbonyl-N-methylcarbamoyl chloride is added dropwise or portionwise with stirring. After stirring for about 2–4 hours in the cold, the reaction mixture is allowed to warm to room temperature. The product is preferably isolated via extraction with an organic solvent such as ethyl acetate. The reaction mixture is poured into a mixture of ethyl acetate and water, the aqueous phase is separated, acidified, and the product extracted with ethyl acetate.

The compounds of the formula I wherein R′ is hydrogen are prepared by acylating the α-amino cephalosporin starting material II with a p-nitrophenyl carbamate

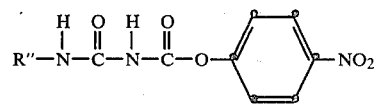

wherein R″ has the previously define meanings. These esters are prepared by reacting urea or the mono-substituted urea, R″—NH—C(O)—NH₂ in an inert solvent such as THF with p-nitrophenyl chloroformate. For example, methylurea is reacted in dry THF at about 0° C. with p-nitrophenyl chloroformate to form p-nitrophenyl N-(methylcarbamoyl)carbamate.

As is the case in the preparation of the above described carbamoyl chlorides, the reaction of urea or a mono-substituted urea with p-nitrophenyl chloroformate affords two isomeric p-nitrophenyl carbamates.

The desired carbamate is formed by the acylation of the $N_1$(unsubstituted)urea nitrogen while the undesired carbamate ester is formed by the acylation of the $N_3$(substituted), or the

urea nitrogen. Usually the two products are formed in equal amounts.

The desired p-nitrophenyl N-(substituted carbamoyl) carbamates form isocyanates when treated with silylating agents such as bis-(trimethylsilyl)acetamide (BSA) or mono(trimethylsilyl)acetamide (MSA). The reaction has been previously described in *Angew. Chem. Int. Ed.*, 7(1968), 941 and is illustrated by the scheme:

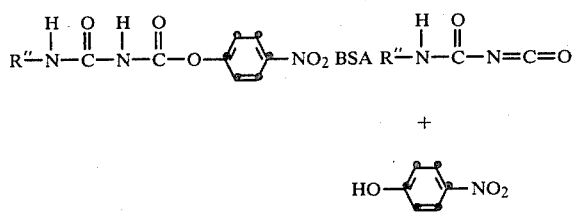

The undesired p-nitrophenyl carbamate

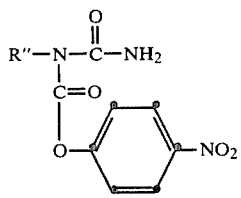

formed along with the above desired carbamate is incapable of forming an isocyanate with the silylating agent.

In the acylation of an α-aminoarylacetamido cephalosporin, II, to form the cephalosporin I wherein R′=H, the mixture of both carbamates obtained as described above is conveniently used. The acylation reaction is carried out in an inert dry solvent in the presence of an excess of a silylating agent such as BSA or MSA. The p-nitrophenyl N-(substituted carbamoyl)carbamate forms the isocyanate in situ which then reacts with the α-amino group of II to form the product.

Illustrative p-nitrophenyl carbamates useful in preparing the compounds of the formula I wherein R′=H are p-nitrophenyl N-(ethylcarbamoyl)carbamate, p-nitrophenyl N-(cyclopropylcarbamoyl)carbamate, p-nitrophenyl N-(phenylcarbamoyl)carbamate, p-nitrophenyl N-(phenylcarbamoyl)-carbamate, p-nitrophenyl N-(propargylcarbamoyl)carbamate, p-nitrophenyl N-(allylcarbamoyl)carbamate, p-nitrophenyl N-(benzylcarbamoyl)carbamate and p-nitrophenyl N-(carbamoyl)-carbamate (R″=H).

The acylation of an α-aminoarylacetamido cephalosporin, II, with the above p-nitrophenyl carbamates is conveniently carried out in dry acetonitrile at about room temperature (20°-25° C.). In order to insure anhydrous conditions the acylation is preferably carried out in an atmosphere of a dry inert gas such as nitrogen or argon. A silylating agent such as BSA or MSA is added in excess and serves two functions. It first serves to solubilize the α-aminoarylacetamidocephalosporin II via formation of soluble silyl derivatives (for example a silyl ester of II) and secondly the excess reacts with the p-nitrophenyl carbamate to generate, in situ, the isocyanate as described above.

The acylation reaction is carried out as follows. A suspension of the α-aminoarylacetamido-cephalosporin II, in dry acetonitrile is treated with excess BSA. After a homogeneous solution is obtained the mixture of p-nitrophenyl carbamates is added in an amount sufficient to provide at least one molar equivalent of the desired p-nitrophenyl carbamate isomer per compound II.

The reaction mixture is stirred at room temperature for between 1 and 3 hours after which the product is recovered.

The cephalosporin product (formula I, R′=H, R₃=H) is conveniently recovered by extracting the reaction mixture, after dilution with water, with a water-immiscible organic solvent such as ethyl acetate, amyl acetate or other suitable solvent. The extraction is carried out at acid pH and preferably at about pH 2.5. The extract is washed, dried and evaporated to yield the cephalosporin antibiotic of the invention.

In an exemplary preparation of the cephalosporins of the formula I wherein R′ is hydrogen, 7-[α-amino-α-(2-thienyl)acetamido]-3-(5-methyl-1,3,4-thiadiazole-2-ylthiomethyl)-3-cephem-4-carboxylic acid is reacted in dry acetonitrile in the presence of excess bis-(trimethylsilyl)-acetamide with p-nitrobenzyl N-(methylcarbamoyl)carbamate to provide, after recovery, 7-[α-(3-methylcarbamoyl-1-ureido)-α-(2-thienyl)acetamido]-3-(5-methyl-1,3,4-thiadiazole-2-yl-thiomethyl)-3-cephem-4-carboxylic acid.

According to the above described preparative procedures the compounds of the formula I wherein R is a 1,3-disubstituted ureido group of the formula

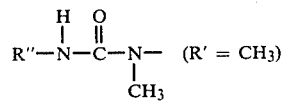

are prepared with the above described carbamoyl chlorides. The compounds I, wherein R′ is hydrogen, are prepared as described above with a p-nitrophenyl N-(substituted carbamoyl) carbamate,

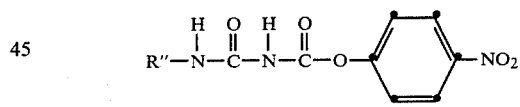

Illustrative of the cephalosporin antibiotics of the formula I wherein R₃ is hydrogen are the following.

| R | R₁ | R₂ |
|---|---|---|
| $\begin{array}{c} H\ \ O \\ |\ \ \| \\ CH_3N-C-N- \\ | \\ CH_3 \end{array}$ | phenyl | $\begin{array}{c} N\text{———}N \\ \|\ \ \ \ \ \ \ \ \| \\ -S\diagdown\ \ \diagup N \\ \ \ \ \ \ \ \ N \\ \ \ \ \ \ \ \ \| \\ \ \ \ \ \ \ \ CH_3 \end{array}$ |
| " | 4-hydroxyphenyl | " |
| " | 4-chlorophenyl | " |
| " | 4-hydroxy-3-chlorophenyl | " |
| " | 2-thienyl | " |
| " | 2-furyl | " |
| " | 3-thienyl | " |

-continued

| R | R₁ | R₂ |
|---|---|---|
| " | phenyl | -S-[1,3,4-thiadiazol-2-yl]-CH₃ (N=N, S ring with CH₃) |
| " | 4-hydroxyphenyl | " |
| " | 2-thienyl | " |
| [imidazolidinone: H-N(C=O)N-] | phenyl | -S-[1-methyl-tetrazol-5-yl] (N=N, N=N, N-CH₃) |
| " | 3-hydroxyphenyl | " |
| " | 2-thienyl | " |
| " | 3-chlorophenyl | " |
| " | phenyl | " |
| " | 4-hydroxyphenyl | " |
| [tetrahydropyrimidinone: H-N(C=O)N-] | phenyl | -S-[thiadiazolyl]-CH₃ |
| " | 3-chloro-4-hydroxyphenyl | " |
| " | 2-thienyl | " |
| " | 2-furyl | " |
| " | phenyl | acetoxy |
| " | 4-hydroxyphenyl | " |
| " | 2-thienyl | " |
| [CH₃-C(=O)-N(C=O)N-] | phenyl | acetoxy |
| " | 4-hydroxyphenyl | [1-methyl-tetrazol-5-yl-thio] |
| [CH₃-SO₂-N(C=O)N-] | phenyl | " |
| " | 2-thienyl | " |
| " | 2-furyl | " |
| [CH₃-SO₂-N(C=O)N- six-membered] | phenyl | " |
| " | " | acetoxy |
| " | 4-hydroxyphenyl | " |
| " | " | [thiadiazolyl-CH₃] |

-continued

| R | R₁ | R₂ |
|---|---|---|
| CH₃-NH-C(=O)-N(CH₃)- | phenyl | acetoxy |
| " | 4-hydroxyphenyl | " |
| " | 3-chloro-4-hydroxyphenyl | " |
| " | 2-thienyl | " |

| (R″) | (R′) | R₁ | R₂ |
|---|---|---|---|
| phenyl | H | phenyl | [thiadiazol-CH₃] |
| " | CH₃ | " | acetoxy |
| benzyl | H | " | [1-methyl-tetrazol-5-yl-thio] |
| 2-furfuryl | H | 4-hydroxyphenyl | " |
| allyl | H | phenyl | " |
| " | CH₃ | " | acetoxy |
| propargyl | H | 3-chloro-4-hydroxyphenyl | " |
| " | H | 2-thienyl | " |
| " | CH₃ | " | [1-methyl-tetrazol-5-yl-thio] |
| " | H | phenyl | " |
| cyclopropyl | H | " | " |
| " | H | " | acetoxy |
| " | CH₃ | " | " |
| cyclopentyl | H | " | " |
| " | H | 4-chlorophenyl | [thiadiazol-CH₃] |
| " | H | 4-hydroxyphenyl | " |
| " | CH₃ | phenyl | [1-methyl-tetrazol-5-yl-thio] |

The cephalosporin antibiotics of the formula I wherein R₃ is hydrogen are converted to the acyloxymethyl esters, wherein R₃ is represented by the group

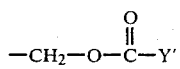

by reacting an alkali metal salt of the cephalosporin carboxylic acid, for example, the lithium, sodium, or potassium salt, with an acyloxymethyl halide of the formula

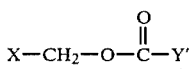

wherein X is chloro or bromo and Y' has the same meanings as previously defined. Acyloxymethyl halides which can be employed include chloromethyl acetate, bromomethyl acetate, bromomethyl propionate, chloromethyl pivaloate, and benzoyloxymethyl chloride.

The preparation of the acyloxymethyl esters of the formula I is carried out by reacting the alkali metal salt form of the parent acid in an inert solvent with a slight molar excess of the bromo or chloromethyl ester, e.g., bromomethyl acetate at room temperature or at slightly elevated temperatures up to about 40°–45° C. Solvents such as acetone, tetrahydrofuran, dioxane, dimethylformamide, and methylene chloride can be used.

The indanyl esters of the formula I wherein $R_3$ is

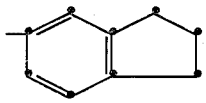

are prepared by reacting 5-indanol in an inert solvent such as dioxane or tetrahydrofuran with the free acid form of a compound of the formula I wherein $R_3$ is hydrogen, in the presence of a condensing agent such as a diimide, for example, dicyclohexyldiimide. The reaction is carried out with stirring at about 20°–35° C. for about 6 to 8 hours. The indanyl ester is isolated by first diluting the reaction mixture with water and filtering the reaction mixture to remove the insoluble dicyclohexylurea. The ester is then extracted from the filtrate.

Alternatively, the indanyl esters can be prepared by reacting a mixed acid anhydride formed with a cephalosporin acid of the formula I and acetic acid with 5-indanol.

The phthalidyl esters of the formula I wherein $R_3$ is the phthalidyl group

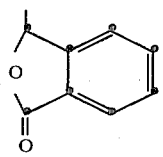

are obtained by reacting bromophthalide of the formula

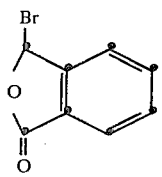

with a salt of a cephalosporin acid of the formula I. The esterification can be carried out in dimethylformamide, dimethylacetamide, dioxane, tetrahydrofuran, or mixtures thereof by slowly warming a mixture of equimolar amounts of the cephalosporin acid salt, for example, the sodium or potassium salt and bromophthalide.

Illustrative esters of the formula I are:

acetoxymethyl 7-[α-(3-methylcarbamoyl-3-methyl-1-ureido)-α-phenylacetamido]-3-(1-methyl-1H-tetrazole-5-ylthio-methyl)-3-cephem-4-carboxylate;

pivaloyloxymethyl 7-[α-(3-methylcarbamoyl-3-methyl-1-ureido]-α-(4-hydroxyphenyl)acetamido]-3-(5-methyl-1,3,4-thiadiazole-2-ylthiomethyl)-3-cephem-4-carboxylate;

phthalidyl 7-[α-(3-methylaminocarbamoyl-3-methyl-1-ureido)-α-phenylacetamido]-3-(1-methyl-1H-tetrazole-5-ylthiomethyl)-3-cephem-4-carboxylate; and acetoxymethyl 7-[α-(3-methylcarbamoyl-3-methyl-1-ureido)-α-(3-chloro-4-hydroxyphenyl)acetamido]-3-(1-methyl-1H-tetrazole-5-ylthiomethyl)-3-cephem-4-carboxylate.

acetoxymethyl 7-[α-(3-methylcarbamoyl-1-ureido)-α-(2-thienyl)acetamido]-3-(1-methyl-1H-tetrazole-5-ylthiomethyl)-3-cephem-4-carboxylate;

pivaloyloxymethyl 7-[α-(3-methylcarbamoyl-1-ureido)-α-phenylacetamido]-3-(1-methyl-1H-tetrazole-5-ylthiomethyl)-3-cephem-4-carboxylate.

The cephalosporin compounds of this invention, in the free acid form (formula I, $R_3$=H), form pharmaceutically acceptable salts with inorganic bases such as the alkali metal carbonates and bicarbonates. For example, the sodium and potassium salts can be formed with sodium and potassium carbonate by following conventional procedures.

Salts can also be prepared with basic organic amines, such as methylamine, diethylamine, cyclohexylamine, dicyclohexylamine, ethanol amine, diethanol amine, and tris-(hydroxymethyl)aminomethane. Such salts can be used to formulate the antibiotics into suitable pharmaceutical forms for parenteral administration.

The cephalosporin antibiotics of this invention are highly effective in inhibiting the growth of a wide spectrum of pathogenic microorganisms of both the gram-positive and gram-negative type.

A number of cephalosporin antibiotics are known which are effective against gram-positive microorganisms but are limited in the spectrum of activity against the gram-negative microorganisms. Other cephalosporin antibiotics which have been synthesized have demonstrated enhanced gram-negative activity; however, they possess either a lower spectrum of activity against the gram-positive organisms or a decreased level of activity against these organisms. The antibiotics described herein have enhanced gram-negative activity both with respect to spectrum and level of activity as well as activity against the gram-positive microorganisms. Thus, the antibiotics described herein can be characterized as cephalosporins having an expanded spectrum of activity.

These cephalosporin antibiotics exhibit high levels of activity against the Pseudomonas, Enterobacter sp., indole (+) and (−), Proteus sp., Aerobacter, Serratia, and Klebsiella gram-negative microorganisms. They also are effective in controlling the growth of penicillin resistant Staphylococcus as well as the Streptococcus D group, e.g., *S. faecalis.*

The antibiotic activity of the cephalosporin compounds of the formula I is illustrated by the data presented in Table I for representative compounds. The values in the table are the minimum inhibitory concentrations (MIC) for the test compounds against the indicated microorganisms. The MIC values were obtained in the Gradient Plate in vitro method for determining antibiotic activity.

I. 7-[α-(3-methylcarbamoyl-1-ureido)-α-(2-thienyl)-acetamido]-3-(1-methyl-1H-tetrazole-5-ylthiomethyl)-3-cephem-4-carboxylic acid.

J. 7-[α-(3-methylcarbamoyl-1-ureido)-α-phenylacetamido]-3-(1-methyl-1H-tetrazole-5-ylthiomethyl)-3-cephem-4-carboxylic acid.

K. 7-[α-(3-methylcarbamoyl-3-methyl-1-ureido)-α-(2-thienyl)acetamido]-3-(1-methyl-1H-tetrazole-5-ylthiomethyl)-3-cephem-4-carboxylic acid.

L. Sodium 7-[α-(3-methylcarbamoyl-1-ureido)-α-(4-hydroxyphenyl)acetamido]-3-(5-methyl-1,3,4-thiadiazole-2-ylthiomethyl)3-cephem-4-carboxylate.

M. 7-[α-(3-phenylcarbamoyl-1-ureido)-α-phenylacetamido]-3-(1-methyl-1H-tetrazole-5-ylthiomethyl)-3-cephem-4-carboxylic acid.

TABLE I

ANTIBIOTIC ACTIVITY OF UREIDO SUBSTITUTED CEPHALOSPORINS

Minimum Inhibitory Concentration (mcg./ml.)
Test Compound[2]

| Test Organism[1] | A | B | C | D | E | F | H | I | J | K | L | M |
|---|---|---|---|---|---|---|---|---|---|---|---|---|
| *Shigella* sp. | 1.0 | 3 | 7 | 7 | 10 | 3 | 9.5 | 3.0 | 4.0 | 1.0 | 5.5 | 4.0 |
| *Escherichia coli* | 1.0 | 4 | 11 | 12 | 18 | 4 | 16 | 5.5 | 7.5 | 2.5 | 7.5 | 10.0 |
| *Klebsiella pneumoniae* | 3.5 | 4 | 14 | 7 | 12 | 1 | 35 | 6.8 | 10 | 0.9 | 16 | 0.6 |
| *Aerobacter aerogenes* | 1.0 | 4 | 14 | 12 | 10 | 3 | 15 | 4.3 | 4.3 | 1.0 | 15.5 | 15.5 |
| *Salmonella heidelberg* | 1.0 | 2 | 13 | 6 | 11 | 3 | 12 | 4.5 | 4.3 | 10 | 6.5 | 7.8 |
| *Pseudomonas aeruginosa* | 18 | 28 | 80 | 90 | 24 | 22 | 60 | 16 | 22.3 | 21.5 | 19.5 | 19.5 |
| *Serratia marcescens* | 8 | 19 | 80 | 70 | 42 | 22 | >200 | 35 | 130 | 19.5 | >200 | 24 |
| V41 | 4.0 | 8 | 1 | 6 | 2 | 5 | 2.5 | 0.6 | 2.0 | 3.0 | 6.5 | 0.6 |
| V32 | 4.8 | 10 | 1 | 7 | 5 | 5 | 4.0 | 0.7 | 3.0 | 3.0 | 7.5 | 0.5 |
| X400 | >20 | >20 | >20 | >20 | >20 | >20 | >20 | 13 | >20 | >20 | >20 | 10.0 |
| V84 | 0.6 | 0.6 | 0.5 | 0.9 | 0.4 | 4 | 1.0 | 0.6 | 5.0 | 3.0 | 0.6 | 0.5 |

[1]Test organisms V41, V32 and V84 are penicillin resistant *Staphyloccus*, X-400 is a methicillin resistant *Staphylococcus*.
[2]Test Compounds:
A. 7-[α-(3-methylcarbamoyl-3-methyl-1-ureido)-α-(4-hydroxyphenyl)acetamido]-3-(1-methyl-1H-tetrazole-5-ylthiomethyl)-3-cephem-4-carboxylic acid.
B. 7-[α-(3-methylcarbamoyl-3-methyl-1-ureido)-α-(4-hydroxyphenyl)acetamido]-3-(5-methyl-1,3,4-thiadiazole-2-ylthiomethyl)-3-cephem-4-carboxylic acid.
C. 7-[α-(3-methylcarbamoyl-3-methyl-1-ureido)-α-phenylacetamido]-3-acetoxymethyl-3-cephem-4-carboxylic acid.
D. 7-[α-(imidazolidine-2-one-1-ylcarbonylamino)-α-phenylacetamido]-3-(1-methyl-1H-tetrazole-5-ylthiomethyl)-3-cephem-4-carboxylic acid.
E. 7-[α-(imidazolidine-2-one-1-ylcarbonylamino)-α-phenylacetamido]-3-acetoxymethyl-3-cephem-4-carboxylic acid.
F. 7-[α-(3-methylcarbamoyl-3-methyl-1-ureido)-α-phenylacetamido]-3-(1-methyl-1H-tetrazole-5-ylthiomethyl)-3-cephem-4-carboxylic acid.
H. 7-[α-(3-carbamoyl-1-ureido-α-phenylacetamido]-3-(1-methyl-1H-tetrazole-5-ylthiomethyl)-3-cephem-4-carboxylic acid.
I. 7-[α-(3-methylcarbamoyl-1-ureido)-α-(2-thienyl)acetamido]-3-(1-methyl-1H-tetrazole-5-ylthiomethyl)-3-cephem-4-carboxylic acid.
J. 7-[α-(3-methylcarbamoyl-1-ureido)-α-phenylacetamido]-3-(1-methyl-1H-tetrazole-5-ylthiomethyl)-3-cephem-4-carboxylic acid.
K. 7-[α-(3-methylcarbamoyl-3-methyl-1-ureido)-α-(2-thienyl)acetamido]-3-(1-methyl-1H-tetrazole-5-ylthiomethyl)-3-cephem-4-carboxylic acid.
L. Sodium 7-[α-(3-methylcarbamoyl-1-ureido)-α-(4-hydroxyphenyl)acetamido]-3-(5-methyl-1,3,4-thiadiazole-2-ylthiomethyl)-3-cephem-4-carboxylate.
M. 7-[α-(3-phenylcarbamoyl-1-ureido)-α-phenylacetamido]-3-(1-methyl-1H-tetrazole-5-ylthiomethyl)-3-cephem-4-carboxylic acid.

A. 7-[α-(3-methylcarbamoyl-3-methyl-1-ureido)-α-(4-hydroxyphenyl)acetamido]-3-(1-methyl-1H-tetrazole-5-ylthiomethyl)-3-cephem-4-carboxylic acid.

B. 7-[α-(3-methylcarbamoyl-3-methyl-1-ureido)-α-(4-hydroxyphenyl)acetamido]-3-(5-methyl-1,3,4-thiadiazole-2-ylthiomethyl)-3-cephem-4-carboxylic acid.

C. 7-[α-(3-methylcarbamoyl-3-methyl-1-ureido)-α-phenylacetamido]-3-acetoxymethyl-3-cephem-4-carboxylic acid.

D. 7-[α-(imidazolidine-2-one-1-ylcarbonylamino)-α-phenylacetamido]-3-(1-methyl-1H-tetrazole-5-ylthiomethyl)-3-cephem-4-carboxylic acid.

E. 7-[α-(imidazolidine-2-one-1-ylcarbonylamino)-α-phenylacetamido]-3-acetoxymethyl-3-cephem-4-carboxylic acid.

F. 7-[α-(3-methylcarbamoyl-3-methyl-1-ureido)-α-phenylacetamido]-3-(1-methyl-1H-tetrazole-5-ylthiomethyl)-3-cephem-4-carboxylic acid.

H. 7-[α-(3-carbamoyl-1-ureido-α-phenylacetamido]-3-(1-methyl-1H-tetrazole-5-ylthiomethyl)-3-cephem-4-carboxylic acid.

In the standard gear agar dilution method, the MIC values for the above test compounds A through E against *Staphylococcus aureus* were as follows: A, 2; B, 1; C, 0.5; D, 2; and E, 0.5 mcg./ml.

The cephalosporin antibiotics of the formula I, wherein $R_3$ is hydrogen, and the pharmaceutically acceptable salts thereof are useful in combating infections in warm blooded mammals when administered parenterally in non-toxic doses between about 10 and 500 mg./kg. The indanyl, phthalidyl and acyloxymethyl esters of the formula I are useful antibiotics when administered orally in non-toxic doses of between about 50 and 750 mg./kg. of body weight.

A preferred group of cephalosporin antibiotics of this invention are represented by the formula I wherein R is

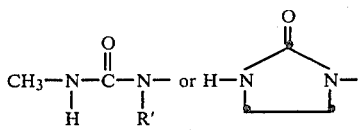

R' is H or methyl;
R₁ is phenyl, hydroxyphenyl, hydroxy-substituted halophenyl, or 2-thienyl;
R₂ is

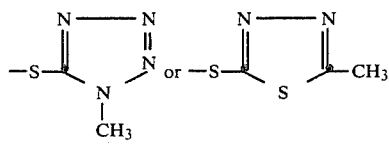

R₃ is hydrogen and the pharmaceutically acceptable salts thereof.

A further preferred group of antibiotics are represented by the formula I when
R is

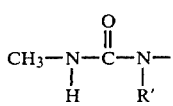

R' is hydrogen or methyl;
R₁ is phenyl, hydroxyphenyl, or hydroxy substituted halophenyl or 2-thienyl;
R₂ is

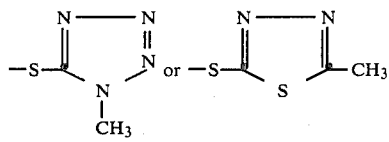

R₃ is hydrogen and the pharmaceutically acceptable non-toxic salts thereof.

Exemplary of the preferred antibiotics are 7-[α-(3-methylcarbamoyl-3-methyl-1-ureido)-α-phenylacetamido]-3-(1-methyl-1H-tetrazole-5-ylthiomethyl)-3-cephem-4-carboxylic acid, 7-[α-(3-methylcarbamoyl-3-methyl-1-ureido)-α-(4-hydroxyphenyl)acetamido]-3-(5-methyl-1,3,4-thiadiazole-2-ylthiomethyl)-3-cephem-4-carboxylic acid;

7-[α-(3-methylcarbamoyl-3-methyl-1-ureido)-α-(4-hydroxyphenyl)acetamido]-3-(1-methyl-1H-tetrazole-2-ylthiomethyl)-3-cephem-4-carboxylic acid, 7-[α-(3-methylcarbamoyl-1-ureido)-α-phenylacetamido]-3-(1-methyl-1H-tetrazole-5-ylthiomethyl)-3-cephem-4-carboxylic acid, 7-[α-(3-methylcarbamoyl-3-methyl-1-ureido)-α-(2-thienyl)acetamido]-3-(1-methyl-1H-tetrazole-5-ylthiomethyl)-3-cephem-4-carboxylic acid, 7-[α-(3-methylcarbamoyl-1-ureido)-α-(2-thienyl)-acetamido]-3-(1-methyl-1H-tetrazole-5-ylthiomethyl-3-cephem-4-carboxylic acid.

7-[α-(imidazolidine-2-one-1-ylcarbonylamino)-α-phenylacetamido]-3-(1-methyl-1H-tetrazole-5-ylthiomethyl)-3-cephem-4-carboxylic acid, 7-[α(3-methylcarbamoyl-3-methyl-1-ureido)-α-(3-chloro-4-hydroxyphenyl)acetamido]-3-(1-methyl-1H-tetrazole-5-ylthiomethyl)-3-cephem-4-carboxylic acid.

7-[α-(3-methylcarbamoyl-3-methyl-1-ureido)-α-(3,5-dichloro-4-hydroxyphenyl)acetamido]-3-(1-methyl-1H-tetrazole-5-ylthiomethyl)-3-cephem-4-carboxylic acid, and the pharmaceutically acceptable, non-toxic salts thereof.

The in vivo effective dose (ED₅) in mg./kg. for representative antibiotics of the formula I has been determined in experimental infections in mice. Table II lists the ED₅₀ dose vs. *Streptococcus pyogenes* and *Escherichia coli* infections. In the table, the antibiotics are identified with the R″, R′, and R₁-R₃ terms of Formula I.

TABLE II

| Test Compound | | | | | ED₅₀(mg/kg × 2) i.p. | |
|---|---|---|---|---|---|---|
| R″ | R′ | R₁ | R₂ | R₃ | S. pyogenes | E. coli |
| CH₃ | H | phenyl | tet[1] | H | 0.7 | 72 |
| CH₃ | CH₃ | 4-hydroxy phenyl | tet | H | 0.7 | 72 |
| H | H | phenyl 4-hydroxy | tet | H | 0.7 | <72 |
| CH₃ | H | phenyl | thiad[2] | H | 0.7 | <72 |
| CH₃ | H | 2-thienyl | tet | H | <7.2 | <72 |
| CH₃ | CH₃ | phenyl | acetoxy | H | <7.2 | <7.2 |

[1] tet = 1-methyl-1H-tetrazole-5-ylthio-
[2] thiad = 5-methyl-1,3,4-thiadiazole-2-ylthio-, The following examples are provided to further describe this invention and are not to be construed as limiting thereof.

In the examples the following abbreviations have the meaning indicated below.
BSA—bis-(trimethylsilyl) acetamide;
THS—tetrahydrofuran;
DMF—dimethylformamide;
NMR—nuclear magnetic resonance spectrum;
IR—infrared absorption spectrum;
UV—ultraviolet absorption spectrum.

EXAMPLE 1

N-Methylcarbamoyl-N-methylcarbamoyl chloride

To a cold suspension of 22 g. (0.25 m.) of sym-dimethylurea in dichloroethane was added dropwise with stirring a cold solution of 30 g. (0.3 m.) of phosgene in 90 ml. of dichloroethane. After the addition of the phosgene solution was complete, the reaction mixture was allowed to stir at room temperature for one hour and was then heated to 80° C. and purged with nitrogen for one hour. The reaction mixture was evaporated under reduced pressure and the residual gum was extracted twice with 350 ml. portions of either. The extracts were combined and evaporated to provide 25 g. of the carbamoyl chloride.

EXAMPLE 2

Imidazolidine-2-one-1-ylcarbonyl chloride

To a stirred suspension of 35 g. of 2-imidazolidine in 500 ml. of dry tetrahydrofuran cooled in an ice bath was added a cold solution of 40 g. of phosgene in 100 ml. of dry tetrahydrofuran. The reaction mixture was stirred at room temperature for about 16 hours and was filtered to remove insolubles. The filtrate was concentrated under reduced pressure and the reaction product precipitated from the concentrate on the addition of acetone and petroleum ether. The product was collected by filtration and dried on the filter.

EXAMPLE 3

Preparation of
7-[α-(3-methylcarbamoyl-3-methyl-1-ureido)-α-(4-hydroxyphenyl)acetamido]-3-(1-methyl-1H-tetrazole-5-ylthiomethyl)-3-cephem-4-carboxylic acid To a suspension of 483 mg. (1 mmole) of 7-[D-α-amino-α-(4-hydroxyphenyl)acetamido]-3-(1-methyl-1H-tetrazole-5-ylthiomethyl)-3-cephem-4-carboxylic acid in 8 ml of dry acetonitrile containing 2 ml. of propylene oxide maintained under an atmosphere of dry argon was added 1 ml. of bis-(trimethylsilyl)acetamide. When solution was obtained, the reaction vessel and solution were cooled to 0°–5° C. A solution of 150 mg. (1 mmole) of N-methylaminocarbonyl-N-methylcarbamoyl chloride in 2 ml. of dry acetonitrile was added dropwise to the cold solution with stirring. The reaction mixture was stirred for 2 hours and was allowed to warm to room temperture. The reaction mixture was poured into a mixture of water and ethyl acetate and the pH of the mixture was adjusted to pH 9. The aqueous layer was separated and relayered with fresh ethyl acetate. The pH of the aqueous layer was adjusted to pH 2.5 and the ethyl acetate layer was separated, was washed with brine and dried over sodium sulfate. The dried ethyl acetate solution containing the reaction product was evaporated to dryness in vacuo to obtain the product as a faintly yellow powder. The product was dissolved in ethyl acetate and in part precipitated by adding petroleum ether to the solution. The precipitate of product was filtered and dried to yield 138 mg. Additional product was recovered by evaporation of the filtrate.

NMR (60 MHz., DMSO $d_6$): 9.8 (d, J=7, 1H), 9.3 (d, J=8, 1H), 7.4–6.5 (m, 5H), 5.85–5.50 (g, 1H), 5.50–5.30 (d, J=7, 1H), 4.9 (d, J=5, 1H), 4.3 (broad, 2H), 3.5 (s, 3H), 3.6 (broad, 2H), 3.1 (s, 3H) and 2.65 (d, J=3, 3H) delta.

Elemental analysis (percent) for $C_{22}H_{25}N_9O_7S_2$: Theory: C, 44.66; H, 4.26; N, 21.31; Found: C, 44.32; H, 4.34; N, 19.32.

EXAMPLE 4

Preparation of
7-[α-(3-methylcarbamoyl-3-methyl-1-ureido)-α-(4-hydroxyphenyl)acetamido]-3-(5-methyl-1,3,4-thiadiazole-2-ylthiomethyl)-3-cephem-4-carboxylic acid.

To a suspension of 2.12 g. (4 mmole) of 7-[D-α-amino-α-(4-hydroxyphenyl)acetamido]-3-(5-methyl-1,3,4-thiadiazole-2-ylthiometyl)-3-cephem-4-carboxylic acid in 32 ml. of dry acetonitrile containing 8 ml. of propylene oxide maintained under an atmosphere of dry argon was added 4 ml. of bis-(trimethylsilyl)acetamide with stirring. When solution had occurred, the solution was cooled to 0° C. and 600 mg. (4 mmole) of N-methylaminocarbonyl-N-methylcarbamoyl chloride in 8 ml. of dry acetonitrile were added dropwise with stirring. The reaction mixture was stirred for 2 hours during which time the temperature of the mixture was allowed to rise to room temperature. The reaction mixture was poured into a water-ethyl acetate mixture and the pH of the aqueous layer was adjusted to pH 8.5. The aqueous layer was separated and layered with fresh ethyl acetate. The pH of the aqueous layer was then adjusted to about pH 2.5 and the ethyl acetate layer was separated, washed with brine and dried over sodium sulfate. The dried solution was evaporated to dryness under reduced pressure to yield about 1.6 g. of the product as a light yellow solid. The product was triturated with ethyl acetate and the insoluble product (645 mg.) was filtered. The filtrate was concentrated by evaporation to yield 423 mg. of precipitated product. The latter filtrate was evaporated to dryness to yield 560 mg. The above three product fractions were shown to be the same when chromatographed on silica gel thin layer chromatograms using chloroform:methanol (7:3, v:v) for development and either iodine vapors or ultraviolet light for visualization of the developed plates.

Elemental analysis (percent) for $C_{23}H_{25}N_7O_7S_3$: Theory: C, 45.46; H, 4.15; N, 16.13 Found: C, 45.53; H, 4.47; N, 14.85.

Electrometric tritration in 66 percent DMF showed the presence of two titratable groups:
$pK_a$ 4.8 and 12.2
and an apparent molecular weight as calculated from the titration data of 587 (calculated MW=607). The infrared absorption spectrum (mineral oil mull) showing the characteristic β-lactam carbonyl absorption at about 2920 wave numbers and the NMR spectrum were in agreement with the expected product.

UV absorption spectrum (methanol)

| λ max 303 | $\epsilon = 9,246$ |
|---|---|
| λ max 275 | $\epsilon = 9,273$ |
| λ max 229 | $\epsilon = 16,254$ |

EXAMPLE 5

Preparation of
7-[α-(3-methylcarbamoyl-3-methyl-1-ureido)-α-phenylacetamido]-3-acetoxymethyl-3-cephem-4-carboxylic acid.

The above-named compound was prepared by the reaction of 7-(D-α-amino-α-phenylacetamido)-3-acetoxymethyl-3-cephem-4-carboxylic acid (cephaloglycine) with N-methylaminocarbonyl-N-methylcarbamoyl chloride by following the reaction conditions employed in Example 3. The product (158 mg.) was obtained as a white crystalline solid.

Nuclear magnetic resonance spectrum (60 MHz., DMSO $d_6$): 7.45 (s, 5H), 5.9–5.4 (m, 2H), 5.2–4.4 (m, 3H) 3.5 (broad, 2H), 3.15 (s, 3H), 2.7 (s, 3H) and 2.05 (s, 3H) delta.

EXAMPLE 6

Preparation of
7-[D-α-(imidazolidine-2-one-1-ylcarbonylamino)-α-phenylacetamido]-3-acetoxymethyl-3-cephem-4-carboxylic acid A suspension of 17.66 g. of cephaloglycine dihydrate in 150 ml. of tetrahydrofuran-water (80 percent THF) was cooled in an ice bath and the pH of the suspension was adjusted to 7.8–8.2 by the addition of triethylamine. To the cold (0° C.) suspension was added in small portions 5.94 g. of N-chlorocarbonylimidazolidine-2-one. Throughout the addition of the acid chloride, the pH of the reaction mixture was maintained between 7.5 and 8.0 by adding triethylamine as required. Following the addition of the acid chloride, the rection mixture was stirred at 0° C. for 30 minutes and then at room temperature for another 20 minutes. The reaction mixture (pH 7.5) was diluted with 130 ml. of water and then evaporated to remove most of the THF. The aqueous phase was extracted once with ether and was then layered with ethyl acetate. The pH of the aqueous layer was adjusted to 1.5 to 2.0 with dilute hydrochloric acid. The ethyl acetate layer was separated and was washed with water and dried over magnesium sulfate. Evaporation of the dried ethyl acetate solution under reduced pressure provided the product as an amorphous solid.

EXAMPLE 7

By following the acylation procedures and conditions described by Example 6, 7-(D-α-amino-α-phenylacetamido)-3-(1-methyl-1H-tetrazole-5-ylthiomethyl)-3-cephem-4-carboxylic acid is reacted with N-chlorocarbonylimidazolidine-2-one to provide 7-[D-(α-(imidazolidine-2-one-1-ylcarbonylamino)-α-phenylacetamido]-3-(1-methyl-1H-tetrazole-5-ylthiomethyl)-3-cephem-4-carboxylic acid.

EXAMPLE 8

By following the procedures and by employing the solvents and conditions described in the acylation of Example 6, 7-(D-α-amino-α-phenylacetamido)-3-(5-methyl-1,3,4-thiadiazole-2-ylthiomethyl)-3-cephem-4-carboxylic acid is reacted with chlorocarbonylimidazolidine-2-one to provide 7-[D-α-(imidazolidine-2-one-1-ylcarbonylamino)-α-phenylacetamido]-3-(5-methyl-1,3,4-thiadiazole-2-ylthiomethyl)-3-cephem-4-carboxylic acid.

EXAMPLE 9

Preparation of Sodium 7-[α-(3-methylcarbamoyl-1-ureido)-α-(4-hydroxyphenyl)acetamido]-3-(5-methyl-1,3,4-thiadiazole-2-ylthiomethyl)-3-cephem-4carboxylate To a suspension of 2.88 g. (6 mmole) of sodium 7-[D-α-amino-α-(4-hydroxyphenyl)acetamido]-3-(5-methyl-1,3,4-thiadiazole-2-ylthiomethyl)-3-cephem-4-carboxylate in 48 ml. of dry acetontrile at room temperature were added 6 ml. of BSA. When an homogeneous solution was obtained 5.2 g. of p-nitrophenyl methylcarbamoylcarbamate were added. The reaction mixture was stirred for one hour and was poured into a mixture of water and ethyl acetate. The pH was adjusted to 6 and the ethyl acetate phase was separated and replaced with fresh ethyl acetate. The pH of the aqueous phase was adjusted to pH 2.5. The aqueous layer was separated and discarded. The ethyl acetate phase was washed with dilute hydrochloric acid (pH 2.0) and fresh water was added. The pH was finally adjusted to 5.5 and the aqueous phase lyophilized to yield 1.3 g. of the product as a light yellow powder.

NMR(DMSO-d6): 2.7 (s, 6H, NHCH$_3$ & thiadiazole CH$_3$), 3.5 (broad, 2H, C2-H$_2$), 5.0 (d, J=5, 1H, C6-H), 5.4–5.9 (m, 2H, C7-H & side chain CH), 6.9 (d, J=9, 2H, aromatic) and 7.4 (d, J=9, 2H, aromatic) delta.

EXAMPLE 10

Preparation of Sodium 7-[α-(3-methylcarbamoyl-3-methyl-1-ureido)-α-phenylacetamido]-3-(5-methyl-1,3,4-thiadiazole-2-ylthiomethyl)-3-cephem-4-carboxylate To a suspension of 2.78 g. of sodium 7-(D-α-amino-α-phenylacetamido)-3-(5-methyl-1,3,4-thiadiazole-2-ylthiomethyl)-3-cephem-4-carboxylate in 48 ml of dry acetonitrile containing 12 ml. of propylene oxide were added 6 ml. of bis-(trimethylsilyl)acetamide. When a homogeneous solution was obtained the solution was cooled to about 0° C. and a solution of 6 mmoles of N-methylaminocarbonyl-N-methylcarbamoyl chloride in 12 ml. of dry acetonitrile was added. The reaction mixture was stirred for 2 hours.

The product was recovered by following the work-up procedures described in Example 9 to yield 1.1 g. of the sodium salt.

IR (mull): β-lactam carbonyl absorption at about 2920 cm$^{-1}$.

NMR (DMSO d6): 2.7 (Broad, 6H, NHCH$_3$ & Thiadiazole CH$_3$), 3.1 (s, 3H, N-CH$_3$), 4.4 (Broad, 2H, C(3')H$_2$), 4.9 (d, J=4.5, 1H, C(6)H), 5.4–5.9 (m, 2H, C(7)H & Side Chain CH), 9.4 (d, J=9, 1H, NH) and 10.0 (d, J=7, 1H, NH) delta.

EXAMPLE 11

Preparation of 7-[α-(3-methylcarbamoyl-3-methyl-1-ureido)-α-(2-thienyl)acetamido]-3-(1-methyl-1H-tetrazole-5-ylthiomethyl)-3-cephem-4-carboxylic acid To suspension of 234 mg. of 7-[α-amino-α-(2-thienyl)acetamido]-3-(1-methyl-1H-tetrazole-5-ylthiomethyl)-3-cephem-4-carboxylic acid in 4 ml. of dry acetonitrile containing 1 ml. of propylene oxide was added under argon 0.5 ml. of BSA to form a homogeneous solution. The solution was cooled to 0° C. and a solution of 75 mg. of N-methylaminocarbamoyl-N-methylcarbamoyl chloride in 1 ml. of acetonitrile. The reaction mixture was stirred for 2 hours and was then poured into a mixture of water-ethyl acetate. The pH of the aqueous phase was adjusted to pH 6 and the organic phase separated. Fresh ethyl acetate was added to the aqueous phase and the pH adjusted to 2.5 with dilute hydrochloric acid. The organic phase was separated, dried and evaporated to dryness to yield the product.

Elemental analysis for: C$_{20}$H$_{23}$N$_9$O$_6$S$_3$:; Theory: C, 41.30; H, 3.99; N, 21.68; Found: C, 41.78; H, 4.14; N, 21.73.

UV(methanol): λ max 238, ε 17,475; λ max 270, ε 9,000.

EXAMPLE 12

Preparation of p-nitrophenyl methylcarbamoylcarbamate

Methylurea (3.7 g., 50 mmole) and p-nitrophenyl chloroformate (50 mmole) were allowed to react under nitrogen in 10 ml. of dry THF. The reaction mixture became clear initially and the product began to precipitate from the clear solution. The mixture was stirred for about 18 hours and the precipitated product was filtered. The product was washed with water and diethyl ether to yield 5.9 g. of approximately a 50:50 mixture of p-nitrophenyl methylcarbamoylcarbamate and p-nitrophenyl carbamoyl-N-methylcarbamate as shown by NMR.

EXAMPLE 13

Preparation of 7-[α-(3-methylcarbamoyl-1-ureido)α-phenylacetamido]-3-(1-methyl-1H-tetrazole-5-ylthiomethyl)-3-cephem-4-carboxylic acid A suspension under argon of 2 mmoles of 7-[(α-amino-α-phenylacetamido]-3-(1-methyl-1H-tetrazole-5-ylthiomethyl)-3-cephem-4-carboxylic acid in 16 ml. of dry acetonitrile was solubilized by adding 2 ml of BSA. With stirring, 4 mmoles of the product mixture obtained as described by Example 12 (mixture of p-nitrophenyl methylcarbamoylcarbamate and p-nitrophenyl carbamoyl-N-methylcarbamate) were added. The reaction mixture became clear in a few minutes and was stirred for about 2 hours.

The reaction mixture was poured into a mixture of water-ethyl acetate and the pH adjusted to 6. The ethyl acetate layer was separated and discarded. The aqueous phase was relayered with fresh ethyl acetate and the pH of the aqueous phase was the adjusted to pH 2.5. The organic layer was separated, washed with water, dried and evaporated in vacuo. The product residue was triturated with diethyl ether to yield 600 mg. of product as a faintly yellow powder.

Elemental analysis for: $C_{21}H_{23}N_9O_6S_2$: Theory: C, 44.91; H, 4.13; 22.45; S, 11.42; Found: C, 44.66; H, 4.34; 22.29; S, 11.28.

UV(methanol): $\lambda$ max 272, $\epsilon$ 11,091.

NMR (DMSO d6): 2.6 (d, J5H$_2$, 3H, NHCH$_3$), 3.9 (S, 3H), —CH$_3$ on tetrazole), 3.55 (Broad, 2H, CH$_2$), 5.0 (d, J=5, 1H, C(6)H), 5.4–5.9 (m, 2H, C(7)H & Side Chain CH), 7.3 (S, 5H, Q), 8.4 (d, J=7, 1H, NH), 8.8 (S, 1H, NH) and 9.4 (d, J=9, 1H, NH) delta.

EXAMPLE 14

Preparation of 7-[α-(3-methylcarbamoyl-1-ureido)-α-(4-hydroxyphenyl)acetamido]-3-(5-methyl-1,3,4-thiadiazole-2-ylthiomethyl)-3-cephem-4-carboxylic acid To a suspension of 988 mg. (2 mmole) of 7-[α-amino-α-(4-hydroxyphenyl)acetamido]-3-(5-methyl-1,3,4-thiadiazole-2-ylthiomethyl)-3-cephem-4-carboxylic acid in 16 ml. of dry acetonitrile were added 2 ml. of BSA under argon. An homogeneous solution was obtained and 1.43 g. (6 mmole) of the product mixture containing 50% of p-nitrophenyl methylcarbamoylcarbamate (Example 12) were added. After stirring for one hour the product was recovered from the reaction mixture by following the work-up procedures described in Example 13. The product, 524 mg., was obtained as a light yellow powder.

UV(methanol): $\lambda$ max 232, $\epsilon$ 16,072; $\lambda$ max 275, $\epsilon$ 14,309.

IR(mull): β-lactam carbanyl absorption at about 2900 cm$^{-1}$.

EXAMPLE 15

Preparation of 7-[α-(3-methylcarbamoyl-1-ureido)-α-(2-thienyl)acetamido]-3-(1-methyl-1H-tetrazole-5-ylthiomethyl)-3-cephem-4-carboxylic acid To a suspension of 435 mg. (0.93 mmole) of 7-[D-α-amino-α-(2-thienyl)acetamido]-3-(1-methyl-1H-tetrazole-5-yl-thiomethyl)-3-cephem-4-carboxylic acid in 8 ml. of dry acetonitrile was added 1 ml. of bis-(trimethylsilyl)acetamide. After an homogeneous solution was obtained 1.4 g. of p-nitrophenyl methylcarbamoylcarbamate were added.

The reaction mixture was stirred at room temperature for 90 minutes. The product was recovered from the reaction mixture by following the work-up procedures described in Example 11. The product was obtained as a white powder weighing 341 mg.

Elemental analysis for: $C_{29}H_{21}N_9O_6S_3$: Theory: C, 40.20; H, 3.73; N, 22.21; S, 16.95; Found: C, 39.86; H, 4.02; N, 22.88; S, 14.66.

I.R. (mull) β-lactam carbonyl absorption at about 2920 cm$^{-1}$.

U.V.(methanol): $\lambda$ max 235, $\epsilon$ 15,459; $\lambda$ max 272, $\epsilon$ 9,360.

NMR(DMSO d6): 2.6(d, J=4.5, 3H, NHCH$_3$), 3.6 (Broad, 2H, C(2)H$_2$), 3.9 (S, 3H, tetrazole CH$_3$), 4.25 (Broad, 2H, C(3')H$_2$), 5.1 (d, J=5, 1H, C(6)H), 5.6–5.9(m, 2H, C(7)H & Side Chain CH), 6.9–7.6(m, 4H, Thiophene & 1NH), 8.4 (d, J=8, 1H, NH), 8.9 (S, 1H, NH) and 9.5 (d, J=8.5, 1H, NH) delta.

EXAMPLE 16

Preparation of p-nitrophenyl phenylcarbamoylcarbamate

To a stirred solution of 6.8 g. of phenylurea in 50 ml. of dry THF maintained at 0° C. under nitrogen were added 5.05 g. of p-nitrophenyl chloroformate. The reaction mixture was allowed to warm to room temperture and was stirred for about 18 hours. The mixture was evaporated to dryness and the residue dissolved in ethyl acetate. The solution was washed twice with water, twice with brine, and was filtered through sodium sulfate. The filtrate was evaporated to dryness to yield 4.9 g. of the product as a white product.

EXAMPLE 17

Preparation of 7-[α-(3-phenylcarbamoyl-1-ureido)-α-phenylacetamido]-3-(1methyl-1H-tetrazole-5-ylthiomethyl)-3-cephem-4-carboxylic acid.

A suspension of 950 mg. (2 mmole) of 7-(D-α-amino-α-phenylacetamido)-3-(1-methyl-1H-tetrazole-5-ylthiomethyl)-3-cephem-4-carboxylic acid in 16 ml. of dry acetonitrile at 0° C. was solubilized under nitrogen with 2 ml. of BSA. With stirring 1.2 g. of p-nitrophenyl N-phenylcarbamoylcarbamate, prepared as described in Example 16, were added to the solution. The reaction mixture was stirred for one hour and the product recovered by following the work-up procedures described in Example 11. The product was obtained as a light yellow powder weighing 839 mg.

NMR(DMSO d6): 3.6 (Broad, 2H C(2)—H$_2$), 3.95 (S, 3H, Tetrazole—CH$_3$), 4.3 (Broad, 2H, C(3')—H$_2$), 5.0 (d, J=5, 1H, C(6)—H), 5.5–5.9 (m, 2H, C(7)—H & Side Chain CH), 7.0–7.6 (Broad, 10H, Aromatic), 8.4 (d, J=7.5, 1H, NH), 9.1 (s, 1H, NH), 9.6 (d, J=9, 1H, NH), 9.8 (S, 1H, NH).

EXAMPLE 18

Preparation of 7-[α-(3-benzylcarbamoyl-1-ureido)-α-phenylacetamido]-3-(1-methyl-1H-tetrazole-5-ylthiomethyl)-3-cephem-4-carboxylic acid By following the procedure described in Example 17, 2 mmoles of 7-(α-amino-α-phenylacetamido)-3-(1-methyl-1H-tetrazole-5-ylthiomethyl)-3-cephem-4-carboxylic acid were dissolved in acetonitrile with BSA and reacted with 1.26 g. of p-nitrophenyl N-benzylcarbamoylcarbamate to yield the title compound.

NMR(DMSO d6): 3.6(Broad, 2H, C(3)H$_2$), 3.9(S, 3H, Tetrazole CH$_3$), 4.3 (Broad, 4H, C(3')—H$_2$ and benzyl CH$_2$), 5.0 (d, J=5, 1H, C(6)H), 5.4–5.9 (m, 2H, C(7)H & Side Chain CH), 7.2–7.6 (m, 10H, Aromatic), 7.8 (t, J=5.5, 1H), 8.4 (d, J=7, 1H, NH), 8.95 (S, 1H, NH), 9.5 (d, J=8, 1H, NH).

EXAMPLE 19

Preparation of 7-[α-(3-furfurylcarbamoyl-1-ureido)-α-phenylacetamido]-3-(1-methyl-1H-tetrazole-5-ylthiomethyl)-3-cephem-4-carboxylic acid By following the procedure described in Example 17, 2 mmoles of 7-(α-amino-α-phenylacetamido)-3-(1-methyl-1H-tetrazole-5-ylthiomethyl)-3-cephem-4-carboxylic acid were reacted at 0° C. in dry acetonitrile with BSA and 1.22 g. of p-nitrophenyl N-furfurylcarbamoylcarbamate to obtain the title compound.

NMR(DMSO d6): 3.55 (Broad, 2H, C(2)-H$_2$), 3.9 (S, 3H, Tetrazole CH$_3$), 4.3 (Broad, 4H, C(3')H$_2$ & Thiophene CH$_2$), 5.0 (d, J=5, 1H, C(6)H), 5.4–5.9 (m, 2H, C(7)-H & Side Chain CH), 6.3 (m, 2H, thiophene aromatic), 7.2–7.9 (m, 7H, aromatic & NH), 8.4 (d, J=7, 1H, NH), 8.9 (s, 1H, NH), 9.4 (d, J=8, 1H, NH).

EXAMPLE 20

Preparation of p-nitrophenyl carbamoylcarbamate

To a mixture of 1.20 g. (20 mmole) of urea and 2.02 g. (10 mmole) of p-nitrophenyl chloroformate in a dry flask under nitrogen were added 10 ml. of dry acetonitrile. The reaction mixture momentarily became clear and then a precipitate formed. The mixture was stirred for 18 hours at room temperature and the precipitate was filtered, washed with water and dried under vacuum. The dried product was triturated with ether and redried to yield 1.0 g. of crystalline product.

EXAMPLE 21

Preparation of 7-[α-(3-carbamoyl-1-ureido)-α-phenylacetamido]-3-(1-methyl-1H-tetrazole-5-ylthiomethyl)-3-cephem-4-carboxylic acid To a suspension of 2 mmole of 7-(α-amino-α-phenylacetamido)-3-(1-methyl-1H-tetrazole-5-ylthiomethyl-3-cephem-4-carboxylic acid in 20 ml. of dry acetonitrile under argon were added ¾ ml. of BSA. When an homogeneous solution was obtained it was evaporated to dryness. The residual dry off-white powder was dissolved in DMF and the solution added under argon with stirring to a solution of 20 mmole of p-nitrophenyl carbamoylcarbamate (Example 20) in 10 ml. of DMF containing 20 mg. of 1-hydroxybenzotriazole monohydrate. The reaction mixture was stirred for 72 hours at room temperature and then was diluted with water and the product extracted with ethyl acetate at a pH of about 2.5. The extract was washed, dried and evaporated to yield the product as an amorphous powder.

Elemental analysis for: C$_{20}$H$_{21}$N$_9$O$_6$S$_2$:

Theory: C, 43.87; H, 3.87; N, 23.02; S, 11.71; Found: C, 43.77; H, 4.00; N, 22.86; S, 11.41.

UV(methanol): λ max 250 ε 8,957.

NMR (DMSO d6): 3.55 (Broad, 2H, C(2)H$_2$), 3.95 (S, 3H, tetrazole—CH$_3$), 4.45 (Broad, 2H, c(3')H$_2$), 5.0(d, J=5, 1H, C(6)H), 5.4–5.9 (m, 2H, C(7)H & Side Chain CH), 6.75 (Broad S, 2H, —NH$_2$) 7.4 (S, 5H, phenyl), 8.51 (d, J=7, 1H, NH), 8.8 (S, 1H, NH) and 9.5 L (d, J=10, 1H, NH) delta.

EXAMPLE 22

Preparation of 3-(methylsulfonyl)imidazolidine-2-one-1-ylcarbonyl chloride

To a suspension of 10.7 g. of imidazolidone-2 in 100 ml. of dry THF were added dropwise with stirring at room temperature 15.7 g. of methanesulfonyl chloride. The reaction mixture was stirred for one-hour at about 40° C. and was then heated at the reflux temperature for one-hour.

The reaction mixture was evaporated in vacuo and the thick syrupy residue was dried in vacuo for about 18 hours. The dried residue was crystallized from warm acetone to yield 7.1 g. of N-methylsulfonyl-imidazolidone-2. The percent elemental composition of the product was determined by microanalysis:

Calculated for: C$_4$H$_8$N$_2$O$_3$S: Theory: C, 29.26; H, 4.91; N, 17.06; S, 19.53; Found: C, 29.47; H, 4.96; N, 17.17; S, 19.50.

A solution of 4.1 g. of the above product in dioxane was treated with 7 g. of trimethylchlorosilane and 5 g. of triethylamine.

The solution was heated at the reflux temperature for about 2.5 days and was cooled to room temperature. The precipitate of triethylamine hydrochloride was filtered and the filtrate treated with 3 ml. of phosgene. The filtrate was allowed to stand at room temperature for 2 days and was evaporated in vacuo to dryness. The residue was crystallized from warm acetone and the product further dried in vacuo to yield 2.8 g. of the title compound melting at about 178° C.

EXAMPLE 23

Preparation of 7-[α-[3-(methylsulfonyl)imidazolidine-2-one-1-ylcarbonylamino]α-(2-thienyl)acetamido]-3-(1-methyl-1H-tetrazole-5-ylthiomethyl)-3-cephem-4-carboxylic acid To a solution of 200 mg. of 7-[α-amino-α-(2-thienyl)acetamido]-3-(1-methyl-1H-tetrazole-5-ylthiomethyl)-3-cephem-4-carboxylic acid in 25 ml. of dichloromethane were added 2 molar equivalents of triethylamine and a pinch of sodium sulfate. The mixture was filtered and 100 mg. of 3-methylsulfonylimidazolidine-2-one-1-ylcarbonyl chloride were added to the filtrate. The reaction mixture was stirred for 3 hours in a water bath after which the dichloromethane was evaporated. The residue was extracted at pH 2 with ethyl acetate and the extract was washed with water and dried. The dried extract was evaporated in vacuo and the residue recrystallized twice from acetone:diethylether:petroleum ether to yield 109 mg. of the product.

UV(methanol): λ max 270, ε 9,328; λ max 233, ε 15,995.

NMR(DMSO d6): 3.45 (S, 3H, CH$_3$SO$_2$—), 3.65 (AB, 2H, C(2)—H$_2$), 3.8(Broad, 4H, CH$_2$CH$_2$), 3.95 (S, 3H, tetrazole CH$_3$), 4.6 (AB, 2H, C(3')—H$_2$), 5.05 (d, J=5, 1H, C(6)—H), 5.75 (dd, J=8, J$_2$=5, 1H, C(7)—H), 5.88 (d, J=7.5, 1H, Side Chain CH), 6.94–7.15 (m, 2H, thiophene aromatic), 7.4–7.5 (dd, 1H, thiophene aromatic), 8.72 (d, J=7, 1H, NH) and 9.51 (d, J=8.5, 1H, NH) delta.

Following the preparative methods described in the above examples, 7-[α-(3-methylcarbamoyl-3-methyl-1-ureido)-α-(4-hydroxyphenyl)acetamido]-3-(1-methyl-1,2,3-triazole-5-ylthiomethyl)-3-cephem-4-carboxylic acid and 7-]D-α-(imidazolidine-2-one-1-ylcarbonylamino)-α-phenylacetamdio]-3-(1-methyl-1,2,3-triazole-5-ylthiomethyl)-3-cephem-4-carboxylic acid are prepared.

We claim:

1. The compound of the formula

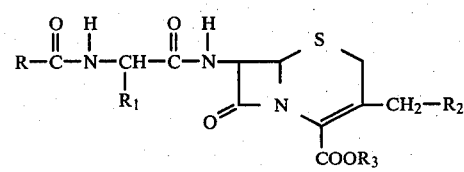

wherein

R is a 3-substituted ureido group represented by the formula

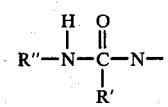

wherein R'' is hydrogen, $C_1$–$C_3$ alkyl, allyl, propargyl, $C_3$–$C_6$ cycloalkyl, phenyl, benzyl, or furfuryl; R' is hydrogen or methyl;

$R_1$ is phenyl, mono or dihydroxyphenyl, mono or dihalophenyl, monohydroxy substituted mono or dihalophenyl, or

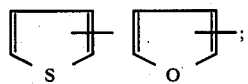

$R_2$ is acetoxy,

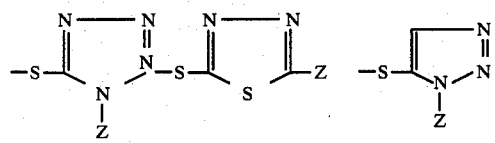

wherein Z is $C_1$–$C_4$ lower alkyl;

$R_3$ is hydrogen, indanyl, phthalidyl, or an acyloxymethyl group of the formula

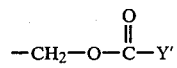

wherein Y' is $C_1$–$C_4$ alkyl or phenyl; and when $R_3$ is hydrogen, the pharmaceutically acceptable nontoxic salts thereof.

2. The compound of claim 1 wherein R' is methyl.
3. A compound of claim 2 of the formula:

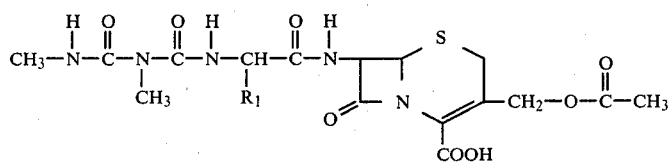

wherein $R_1$ is phenyl, hydroxyphenyl, hydroxy-substituted-chlorophenyl or 2-thienyl, and the pharmaceutically acceptable salts thereof.

4. A compound of claim 2 of the formula:

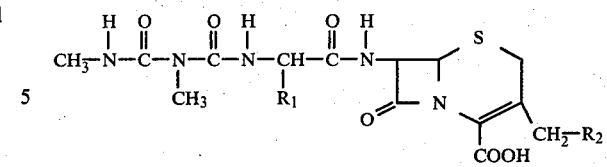

wherein $R_1$ is phenyl, hydroxyphenyl, hydroxy-substituted chlorophenyl or 2-thienyl;

$R_2$ is 1-methyl-1H-tetrazol-5-ylthio or 2-methyl-1,3,4-thiadiazol-5-ylthio, and the pharmaceutically acceptable salts thereof.

5. The compound of claim 4, said compound being 7-[α-(3-methylcarbamoyl-3-methyl-1-ureido)-α-phenylacetamido]-3-(1-methyl-1H-tetrazole-5-ylthiomethyl)-3-cephem-4-carboxylic acid.

6. The compound of claim 4, said compound being 7-[α-(3-methylcarbamoyl-3-methyl-1-ureido)-α-(4-hydroxyphenyl) acetamido]-3-(1-methyl-1H-tetrazole-5-ylthiomethyl)-3-cephem-4-carboxylic acid.

7. The compound of claim 4, said compound being 7-[α-(3-methylcarbamoyl-3-methyl-1-ureido)-α-phenylacetamido]-3-(5-methyl-1,3,4-thiadiazole-2-ylthiomethyl)-3-cephem-4-carboxylic acid.

8. The compound of claim 4, said compound being 7-[α(3-methylcarbamoyl-3-methyl-1-ureido)-α-(4-hydroxyphenyl)acetamido]-3-(5-methyl-1,3,4-thiadiazole-2-ylthiomethyl)-3-cephem-4-carboxylic acid.

9. The compound of claim 4 said compound being 7-[α-(3-methylcarbamoyl-3-methyl-1-ureido)-α-(2-thienyl)-acetamido]-3-(1-methyl-1H-tetrazole-5-ylthiomethyl)-3-cephem-4-carboxylic acid.

10. The compound of claim 1 wherein R' is hydrogen.

11. The compound of claim 10 said compound being 7-[α-3-methylcarbamoyl-1-ureido)-α-phenylacetamido]-3-(1-methyl-1H-tetrazole-5-ylthiomethyl)-3-cephem-4-carboxylic acid.

12. The compound of claim 10 said compound being 7-[α-(3-methylcarbamoyl-1-ureido)-α-(2-thienyl)-acetamido]-3-(1-methyl-1H-tetrazole-5-ylthiomethyl)-3-cephem-4-carboxylic acid.

13. The compound of claim 10 said compound being 7-[α-(3-methylcarbamoyl-1-ureido)-α-(4-hydroxyphenyl)-acetamido]-3-(5-methyl-1,3,4-thiadiazole-2-ylthiomethyl)-3-cephem-4-carboxylic acid.

14. A compound of the formula

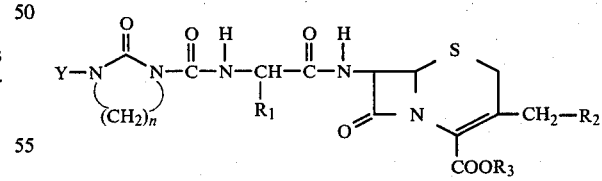

wherein Y is hydrogen, acetyl or methanesulfonyl; n is 2 or 3; $R_1$ is phenyl, mono or dihydroxyphenyl, mono or dihalophenyl, monohydroxy substituted mono or dihalophenyl, or

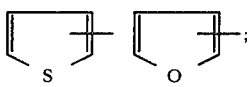

R₂ is

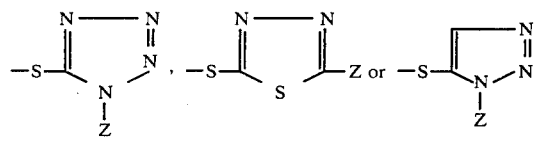

wherein Z is $C_1$-$C_4$ lower alkyl;
R₃ is hydrogen, indanyl, phthalidyl, or an acyloxymethyl group of the formula

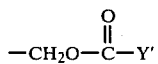

wherein Y' is $C_1$-$C_4$ alkyl or phenyl; and when R₃ is hydrogen, the pharmaceutically acceptable non-toxic salts thereof.

15. A compound of claim 14 of the formula:

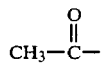

wherein
R is H—, $$CH_3-\overset{O}{\underset{\|}{C}}-$$

or $CH_3$—$SO_2$—;
R₁ is phenyl, hydroxyphenyl, hydroxy-substituted-chlorophenyl or 2-thienyl;
R₂ is 1-methyl-1H-tetrazol-5-ylthio or 2-methyl-1,3,4-thiadiazol-5-ylthio, and
the pharmaceutically acceptable salts thereof.

16. The compound of claim 15, said compound being 7-[α-(imidazolidine-2-one-1-ylcarbonylamino)-α-phenyl-acetamido]-3-(1-methyl-1H-tetrazole-5-ylthiomethyl)-3-cephem-4-carboxylic acid.

17. The compound of claim 15, said compound being 7-[α-(imidazolidine-2-one-1-ylcarbonylamino)-α-phenyl-acetamido]-3-(5-methyl-1,3,4-thiadiazole-2-ylthiomethyl)-3-cephem-4-carboxylic acid.

18. The compound of claim 15, said compound being 7-[α-(imidazolidine-2-one-1-ylcarbonylamino)-α-(4-hydroxyphenyl)acetamido]-3-(1-methyl-1H-tetrazole-5-ylthiomethyl)-3-cephem-4-carboxylic acid.

19. The compound of claim 15, said compound being 7-[α-(imidazolidine-2-one-1-ylcarbonylamino)-α-(4-hydroxyphenyl)acetamido]-3-(5-methyl-1,3,4-thiadiazole-2-ylthiomethyl)-3-cephem-4-carboxylic acid.

20. The compound of claim 15 of the formula

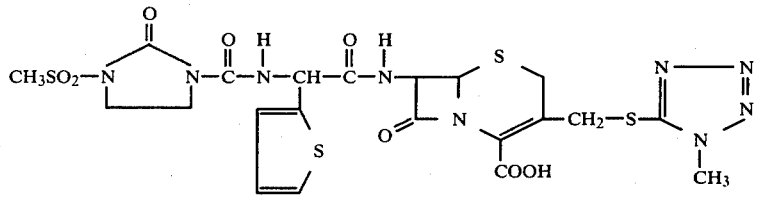

and the pharmaceutically acceptable non-toxic salts thereof.

* * * * *